US011033907B2

(12) United States Patent
Somma et al.

(10) Patent No.: US 11,033,907 B2
(45) Date of Patent: Jun. 15, 2021

(54) METHOD AND APPARATUS FOR SEPARATING PLASTIC AND CELLULOSE FROM POST-CONSUMER ABSORBENT SANITARY PRODUCTS

(71) Applicant: FATER S.p.A., Pescara (IT)

(72) Inventors: Marcello Somma, Pescara (IT); Giorgio Vaccaro, Pescara (IT); Giuseppe Landolfo, Pescara (IT)

(73) Assignee: FATER S.P.A., Pescara (IT)

( * ) Notice: Subject to any disclaimer, the term of this patent is extended or adjusted under 35 U.S.C. 154(b) by 71 days.

(21) Appl. No.: 16/325,162

(22) PCT Filed: Sep. 25, 2017

(86) PCT No.: PCT/IB2017/055798
§ 371 (c)(1),
(2) Date: Feb. 12, 2019

(87) PCT Pub. No.: WO2018/060827
PCT Pub. Date: Apr. 5, 2018

(65) Prior Publication Data
US 2019/0224886 A1    Jul. 25, 2019

(30) Foreign Application Priority Data

Sep. 28, 2016  (IT) .................. 102016000097297

(51) Int. Cl.
*B02C 19/06* (2006.01)
*A61L 2/07* (2006.01)
(Continued)

(52) U.S. Cl.
CPC ................ *B02C 19/06* (2013.01); *A61L 2/07* (2013.01); *A61L 11/00* (2013.01); *B02C 19/186* (2013.01);
(Continued)

(58) Field of Classification Search
CPC ......... B02C 23/18; B02C 23/10; B02C 19/06; B02C 19/186; B09B 3/0091
See application file for complete search history.

(56) References Cited

U.S. PATENT DOCUMENTS 5,292,075 A * 3/1994 Bartlett .................. D21B 1/026
                                                                  241/20
9,393,546 B2 * 7/2016 Ito ............................ B01J 20/22
(Continued)

FOREIGN PATENT DOCUMENTS

EP    0739657 A1    10/1996
EP    2596810 A1    5/2013
(Continued)

OTHER PUBLICATIONS

International Search Report and Written Opinion dated Jan. 10, 2018 for Application No. PCT/IB2017/055798.

*Primary Examiner* — Faye Francis
(74) *Attorney, Agent, or Firm* — Patterson + Sheridan, LLP

(57) ABSTRACT

A method is disclosed for separating plastic and cellulose from post-consumer absorbent sanitary products. The method includes sterilizing successive batches of post-consumer absorbent sanitary products in at least one rotary autoclave. The method further includes shredding the sterilized absorbent sanitary products and obtaining sterilized and shredded material containing plastic and cellulose. The method further includes drying the sterilized and shredded material containing plastic and cellulose, and separating cellulose from plastic from said sterilized, shredded and dried material in at least one centrifugal separator.

7 Claims, 4 Drawing Sheets

(51) Int. Cl.
  *A61L 11/00* (2006.01)
  *B09B 3/00* (2006.01)
  *B29B 17/04* (2006.01)
  *B02C 23/18* (2006.01)
  *B02C 23/10* (2006.01)
  *B02C 19/18* (2006.01)
  *B29B 17/02* (2006.01)
  *B29K 1/00* (2006.01)

(52) U.S. Cl.
  CPC .............. *B02C 23/10* (2013.01); *B02C 23/18* (2013.01); *B09B 3/0075* (2013.01); *B09B 3/0091* (2013.01); *B29B 17/02* (2013.01); *B29B 17/0412* (2013.01); *B29B 2017/0203* (2013.01); *B29B 2017/0231* (2013.01); *B29K 2001/00* (2013.01)

(56) References Cited

U.S. PATENT DOCUMENTS

2013/0153693 A1\* 6/2013 Somma .................. A61L 11/00
  241/5
2015/0360203 A1\* 12/2015 Ito ........................ A01K 1/0155
  502/402

FOREIGN PATENT DOCUMENTS

| EP | 2596811 A1 | 5/2013 |
| JP | H06226137 A | 8/1994 |
| WO | 97/05954 A1 | 2/1997 |
| WO | 98/51139 A2 | 11/1998 |
| WO | 2011/092509 A2 | 8/2011 |

\* cited by examiner

METHOD AND APPARATUS FOR SEPARATING PLASTIC AND CELLULOSE FROM POST-CONSUMER ABSORBENT SANITARY PRODUCTS

FIELD OF THE INVENTION

The present invention relates to recycling of post-consumer absorbent sanitary products.

The term "absorbent sanitary products" generally refers to disposable absorbent products, such as diapers for babies, incontinence pads for adults, sanitary towels, bed linings, etc.

The present invention specifically relates to a method and an apparatus for separating plastic and cellulose from post-consumer absorbent sanitary products.

DESCRIPTION OF THE PRIOR ART

Disposable absorbent sanitary products are generally composed of several materials, including impermeable sheets of plastic material, absorbent elements formed of cellulose fluff and superabsorbent polymers, permeable sheets of non-woven fabric, elastic elements etc. Recycling absorbent sanitary products consists of separating the main products, typically plastic and cellulose.

Methods and apparatuses for recycling absorbent sanitary products are divided into two categories depending on whether they are intended to treat post-production absorbent sanitary products or post-consumer absorbent sanitary products.

Post-production absorbent sanitary products are the waste products of production methods. Separating plastic and cellulose from post-production absorbent sanitary products is typically achieved by shredding post-production absorbent sanitary products and centrifugal separation of plastic and cellulose from the shredded material. Centrifugal separators used for separating plastic and cellulose comprise a perforated drum and a rotor rotating inside the perforated drum, which projects the shredded mass radially outwards. The cellulose fibers are collected outside the perforated drum and the plastic material remains inside the perforated drum and is axially extracted by an airflow produced by rotation of the rotor. An example of a plastic and cellulose separation method from post-production absorbent sanitary products is described in U.S. Pat. No. 9,393,546 B2.

Apparatuses used for separating plastic and cellulose from post-production absorbent sanitary products cannot be used for treating post-consumer absorbent sanitary products because post-consumer absorbent sanitary products contain organic excretions, bacteria, and have a high content of humidity. Recycling post-consumer absorbent sanitary products requires a sterilization step for eliminating bacteria.

Methods for separating plastic and cellulose from post-consumer absorbent sanitary products are known, and they involve washing post-consumer absorbent sanitary products in water, alkali and soap and separating the cellulose from the plastic during washing. Examples of this recycling technique are described in WO94/20668 and WO96/27045.

U.S. Pat. No. 5,292,075 describes a method in which the post-consumer absorbent sanitary products are preliminarily shredded. The shredded material is washed in a washing machine comprising a perforated cylindrical drum that holds the plastic material inside it. The liquid containing the cellulose pulp is collected outside the perforated cylindrical drum and subsequently dehydrated.

EP-A-2596810 by the same Applicant describes a rotary autoclave for sterilizing post-consumer absorbent sanitary products. The autoclave is loaded with post-consumer absorbent sanitary products without prior shredding of the products. The autoclave containing a load of sterilized products is closed and heated to a sterilization temperature by non-contact steam circulating in the autoclave walls and by contact steam that comes into direct contact with the products.

OBJECT AND SUMMARY OF THE INVENTION

The present invention aims to provide a method and an apparatus for separating plastic and cellulose of post-consumer absorbent sanitary products that are more efficient than systems according to the prior art.

According to the present invention, this object is achieved by a method and by an apparatus having the characteristics forming the subject of the claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Figure 1:
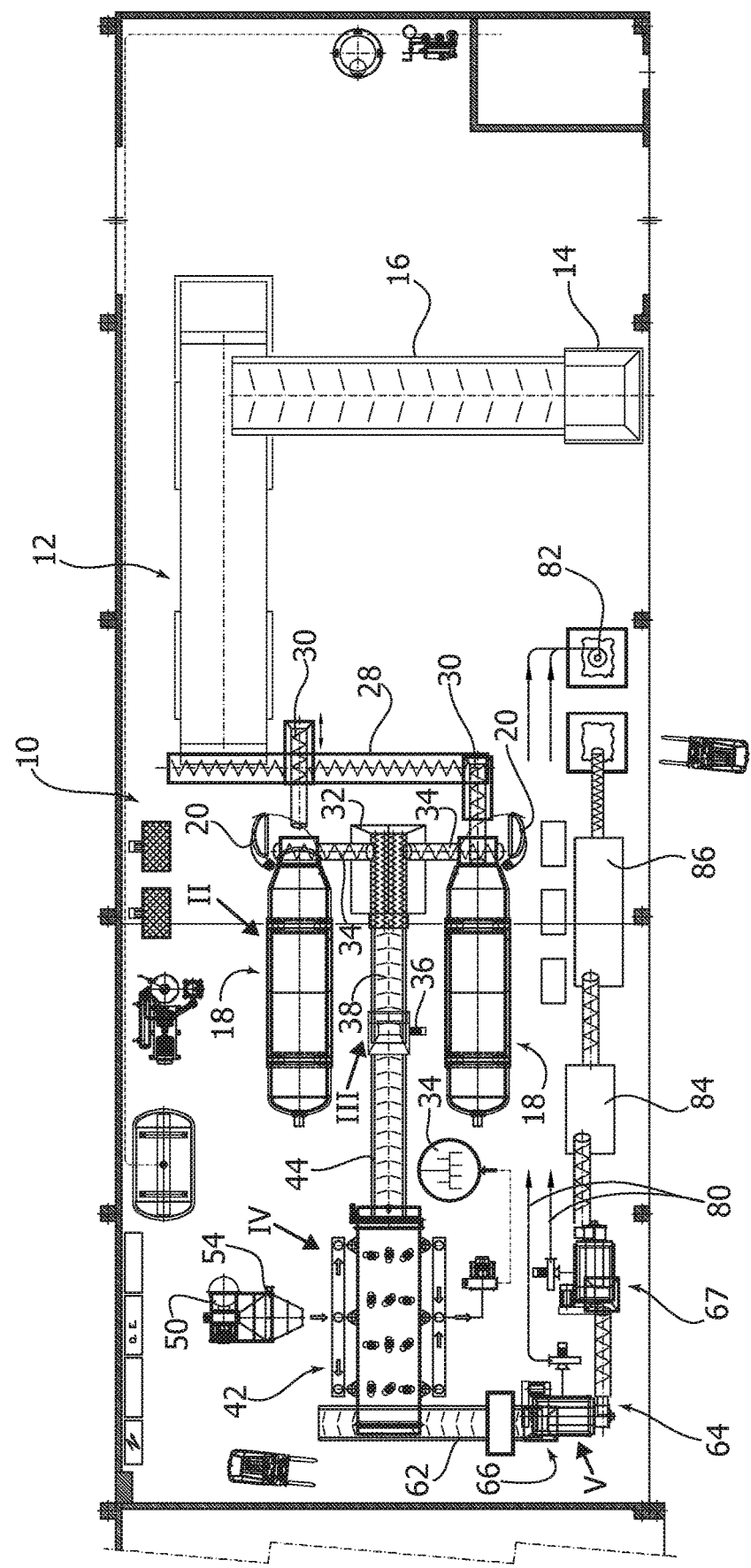
FIG. 1 is a plan view of an apparatus according to the present invention.

FIG. 1 shows an apparatus 10 for separating plastic and cellulose from post-consumer absorbent sanitary articles.

The apparatus 10 comprises a storage container 12 in which post-consumer absorbent sanitary products are collected from the recycling collection. Waste collection vehicles discharge post-consumer absorbent sanitary products into a discharge area 14 and a conveyor 16 loads the post-consumer absorbent sanitary products into the storage container 12. Post-consumer absorbent sanitary products have a density in the order of 150-300 kg/m$^3$ and a humidity content in the order of 65-80%.

Figure 2:
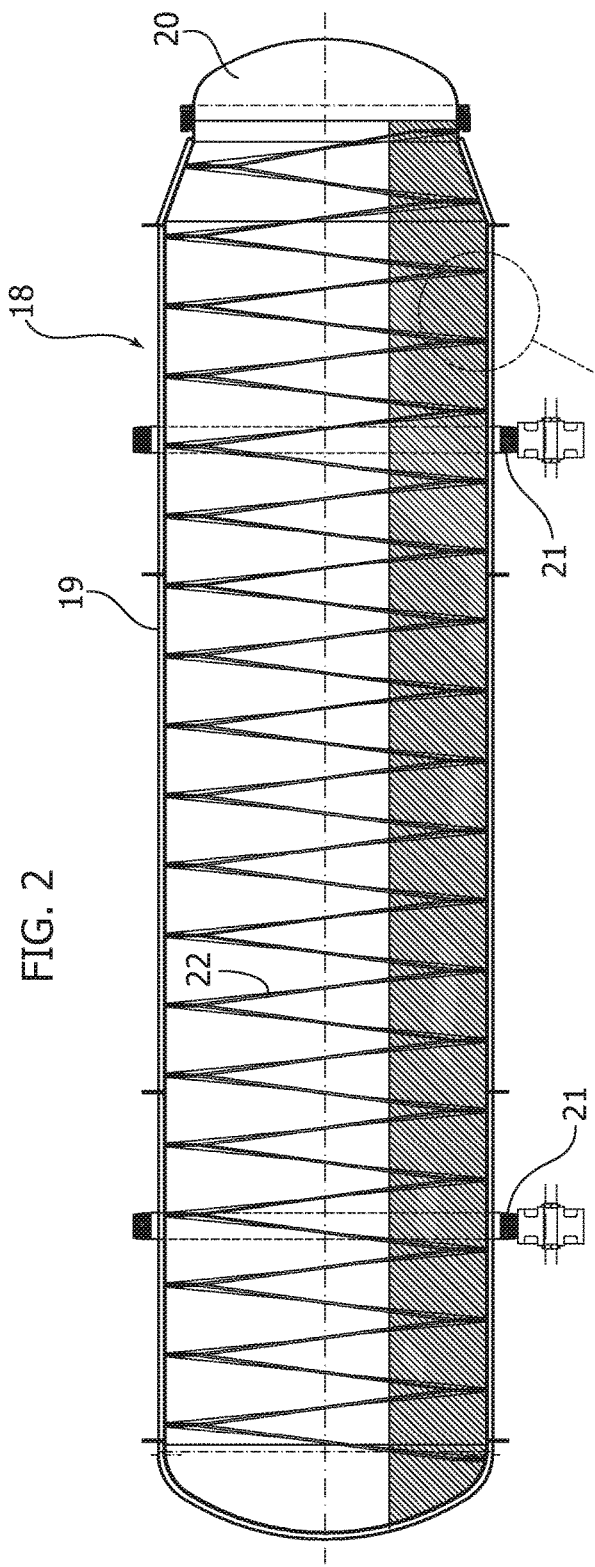
FIG. 2 is a longitudinal cross-section of a rotary autoclave indicated by the arrow II in FIG. 1.
Figure 2A:
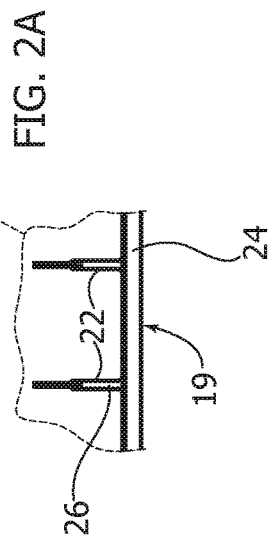
FIG. 2A is an enlarged detail of FIG. 2.

The apparatus 10 comprises at least one rotary autoclave 18 for sterilizing post-consumer absorbent sanitary products. With reference to FIG. 2, the rotary autoclave 18 comprises a cylindrical body 19 elongated along a horizontal axis A and supported in a rotatable manner about the axis A by means of rotating supports 21. The rotary autoclave 18 has a door 20 that can be opened for loading and unloading the products. The inner wall of the autoclave 18 has a helical protruding rib 22 fixed to the cylindrical body 19. As illustrated in detail in FIG. 2A, the body 19 and the helical rib 22 have respective chambers 24, 26 for circulating steam. The body 19 is provided with a rotary manifold (not illustrated) for supplying steam to the chambers 24, 26 of the autoclave 18. The rotary manifold also allows direct injection of steam inside the cylindrical body 19. The rotary manifold is also provided with channels for discharging air and steam from inside the cylindrical body 19 and for extracting condensation from the chambers 24, 26.

In the example illustrated in FIG. 1, the apparatus 10 comprises two autoclaves 18, which are loaded alternately with post-consumer absorbent sanitary products coming from the storage container 12. A conveyor 28 picks up the products from the storage container 12 and transports them towards the autoclave 18. Two loaders 30 load the products into the respective autoclaves 18. During loading of the products, the door 20 is opened and separated from the body 19, and the cylindrical body 19 is rotated about the axis A to progressively shift the products towards the rear. Once loading has finished, the door 20 is closed and the autoclave 18 is heated and pressurized by means of the direct and indirect supply of steam, until it reaches a temperature of about 130° C. and an internal pressure of about 2.5 bar. During the sterilization treatment, the autoclave 18 is alternately rotated clockwise and counterclockwise about the axis A. The sterilization treatment has the object of bringing the temperature of the products to above 121° C., which is the temperature for completely sterilizing the bacteria.

At the end of the sterilization treatment, the steam contained within the autoclave 18 is extracted and purified in a scrubber 34. The door 20 is then opened and the body 19 is rotated to discharge the products. The helical rib 22 acts like a screw that moves the products in the direction of the axis A towards the loading/unloading opening. The sterilized material leaving the autoclaves 18 is collected in a storage vessel 32.

The sterilization treatment of the products in the autoclave 18 is batch-type. In the example of FIG. 1, two autoclaves 18 are provided, which operate in an alternating manner. While a first autoclave 18 performs the sterilization treatment, the other autoclave 18 performs the operations of unloading sterilized material and loading a new batch. In this way, it is possible to obtain an essentially continuous flow of sterilized material downstream of the autoclaves 18.

The sterilized material leaving the autoclaves 18 has a density of about 300-400 kg/m$^3$, a temperature of 80-100° C. and a humidity content in the order of 70-85%.

Figure 3:
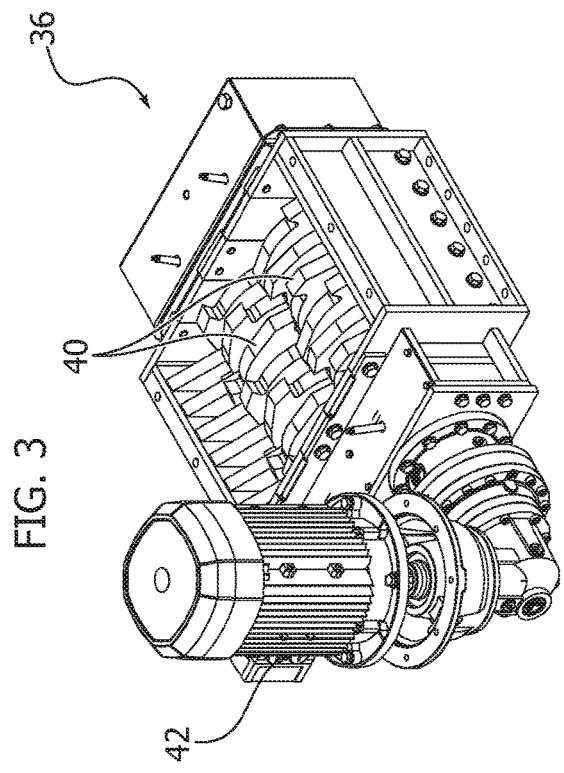
FIG. 3 is a perspective view of a shredder indicated by the arrow III in FIG. 1.

From the storage vessel 32, the sterilized material is sent to a shredder 36 by means of a conveyor belt 38. FIG. 3 illustrates an example of a shredder 36 that can be used to shred sterilized post-consumer absorbent sanitary products. The shredder 36 comprises two rotors 40 driven by a motor 42. The rotors 40 is provided with teeth that carry out shredding of the material. At the outlet of the shredder 36, the material has a density in the order of 400-500 kg/m$^3$, a temperature of about 75-95° C. and a humidity content in the order of 70-85%.

Figure 4:
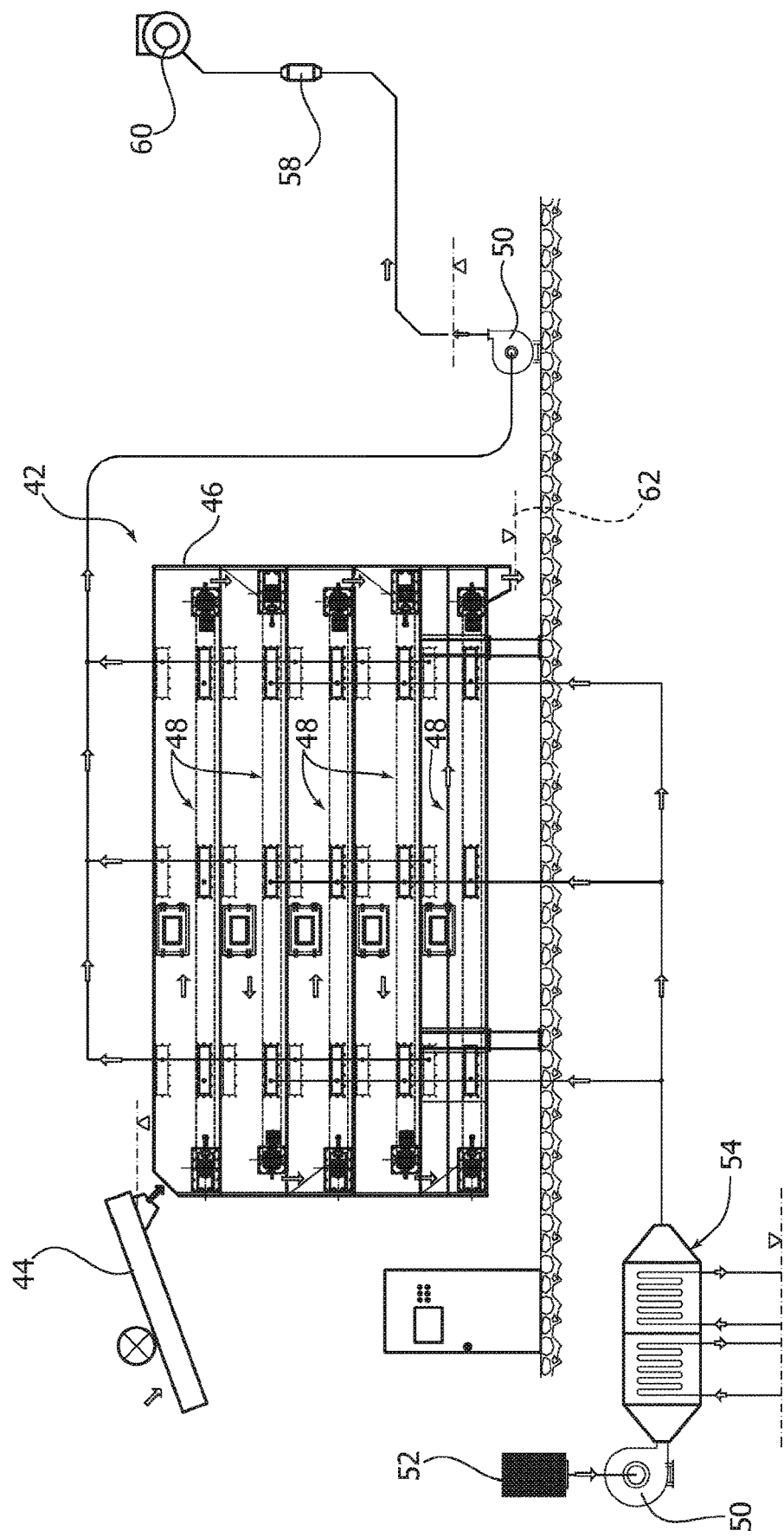
FIG. 4 is a schematic side view of a dryer unit indicated by the arrow IV in FIG. 1.

With reference to FIGS. 1 and 4, the sterilized and shredded material leaving the shredder 36 is sent to a dryer 42 by means of a conveyor 44. The dryer 42 comprises a casing 46 within which horizontal perforated conveyors 48 are housed, driven alternately in opposite directions and superimposed vertically. The conveyor 44 unloads the material onto the upper conveyor 48. At the outlet of each horizontal conveyor 48, the material falls onto the underlying conveyor. While the material is transported horizontally and passes sequentially from one conveyor to the underlying one, a flow of heated air passes through the casing 46 from the bottom upwards. The airflow passes through the perforated conveyors 48 and the material located on them. The airflow is generated by a fan 50 connected to a filter 52. The airflow is heated in a battery of heat exchangers 54 supplied with steam. The airflow leaving the heat exchanger 42 is aspirated by a second fan 56 and is sent to a condensation discharge device 58 and to a scrubber 60. At the outlet of the dryer 42, the material is unloaded onto a conveyor belt 62. The dryer 42 can be equipped with microwave generators facing the upper conveyor 48, to accelerate the heating of the material and to increase the drying effect. The material at the inlet of the dryer has a temperature of about 70-90° C. The temperature of the drying air inside the dryer 42 is about 140° C. The product at the outlet of the dryer 42 has a temperature of about 50-70° C., a density of about 35-50 kg/m$^3$ and a humidity of about 5-20%.

Downstream of the dryer 42, the sterilized, shredded and dried material is sent to a separation unit 64 in which plastic and cellulose separation is performed. The separation unit 64 comprises at least one centrifugal separator. In the example illustrated, two centrifugal separators 66, 67 are provided in cascade.

Figure 5:
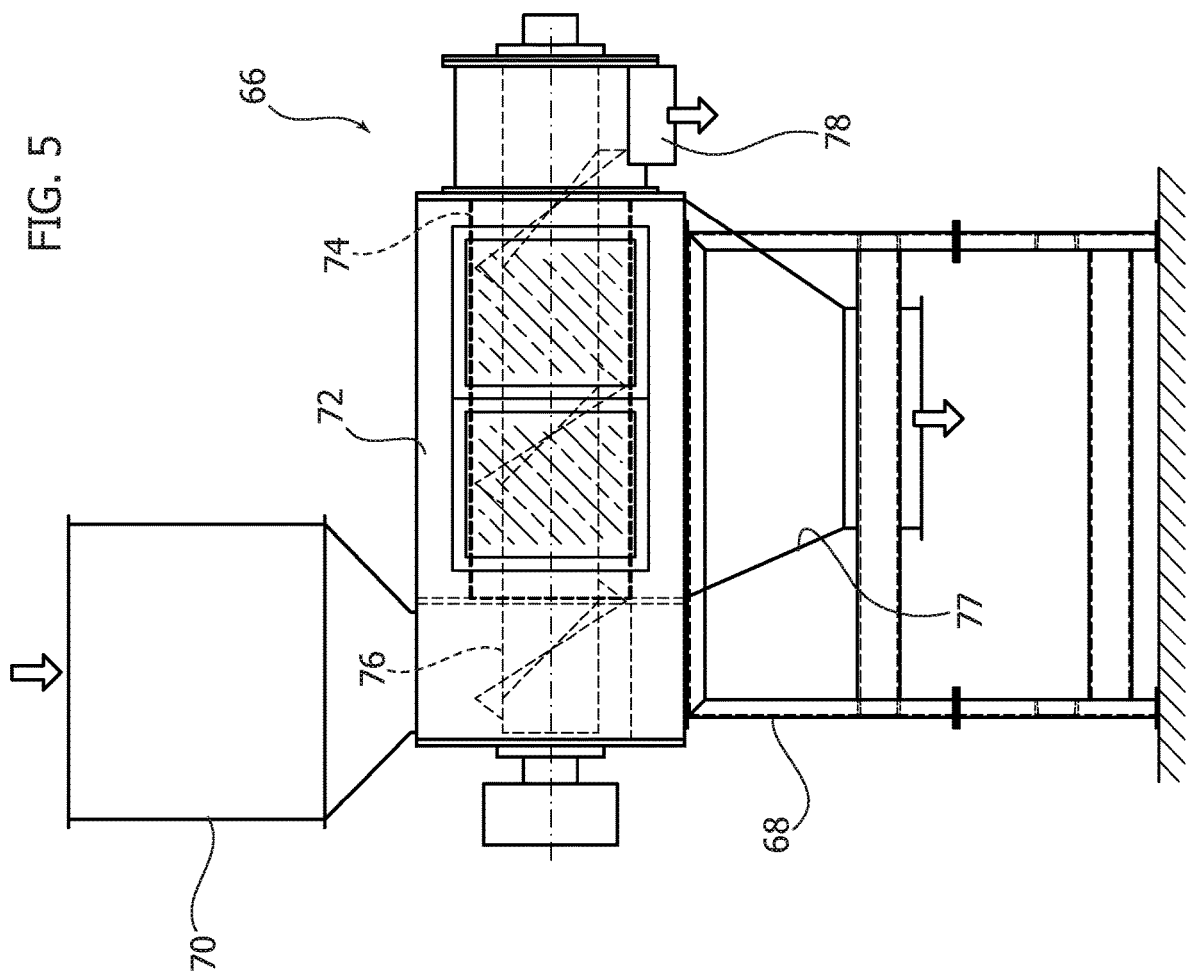
FIG. 5 is a schematic side view of a centrifugal separator indicated by the arrow V in FIG. 1.

With reference to FIG. 5, the centrifugal separator 66 comprises a base 68 having an inlet 70 for the material to be separated. The centrifugal separator 66 comprises a separation chamber 72 in which a perforated cylindrical filter 74 is housed, within which a rotor 76 is mounted, rotatable about a horizontal axis. The inlet material is projected radially from the inside outwards against the perforated filter 74. The cellulose has smaller dimensions than the plastic, and passes through the filter and is collected in a first outlet 77, while the plastic remains inside with respect to the filter 74 and is collected in a second outlet 78. Preferably, the plastic leaving the first centrifugal separator 66 is sent to a second centrifugal separator 67 having a filter with smaller perforations. At the outlet of the first centrifugal separator 66, cellulose is obtained with a purity in the order of 85-95%, and plastic with a purity in the order of 60-80%. At the outlet of the second centrifugal separator, cellulose is obtained with a purity in the order of 85-95% and plastic with a purity in the order of 85-97%.

With reference to FIG. 1, at the outlet of the centrifugal separators 66, the cellulose flows 80 can be sent to a cellulose shredder and to a cellulose pelletizer 82. Alternatively, cellulose flows can be sent to a further separator apparatus for separating cellulose and AGM, to obtain cellulose with a high degree of purity.

The plastic leaving the second shredder 66 can be sent to a plastic shredder 84 and subsequently to an extruder or densifier 86.

Of course, without prejudice to the principle of the invention, the details of construction and the embodiments can be widely varied with respect to those described and illustrated, without thereby departing from the scope of the invention as defined by the claims that follow.

The invention claimed is:

1. A method for separating plastic and cellulose from post-consumer absorbent sanitary products, comprising:
   sterilizing successive batches of post-consumer absorbent sanitary products in at least one rotary autoclave,
   for each batch of the successive batches, after sterilizing the absorbent sanitary products, extracting the sterilized absorbent sanitary products from the at least one rotary autoclave and then shredding the sterilized absorbent sanitary products to obtain sterilized and shredded material containing plastic and cellulose,
   for each batch of the successive batches, after shredding the sterilized and shredded material containing plastic and cellulose, drying the sterilized and shredded material containing plastic and cellulose, and
   for each batch of the successive batches, after drying the sterilized and shredded material containing plastic and cellulose, separating cellulose from plastic from the sterilized, shredded and dried material in at least one centrifugal separator.

2. A method according to claim 1, wherein at the end of the shredding step, the sterilized and shredded material has a humidity between 70-85%.

3. A method according to claim 1, wherein at the end of the shredding step, the sterilized and shredded material has a density between 400-500 kg/m$^3$.

4. A method according to claim 1, wherein at the end of the drying step, the sterilized, shredded and dried material has a humidity between 5-20%.

5. A method according to claim 1, wherein at the end of the drying step, the sterilized, shredded and dried material has a density between 35-50 kg/m$^3$.

6. A method according to claim 1, wherein the at least one centrifugal separator comprises a first centrifugal separator, and wherein the sterilized, shredded and dried material is sent to the first centrifugal separator, at an outlet of which cellulose is obtained with a purity between 85-95% and plastic with a purity between 60-80%.

7. A method according to claim 6, wherein the at least one centrifugal separator further comprises a second centrifugal separator, and wherein the plastic leaving the first centrifugal separator is sent to the second centrifugal separator and wherein at an outlet of said second centrifugal separator cellulose is obtained with a purity between 85-95% and plastic with a purity between 85-97%.

\* \* \* \* \*